US010441547B2

(12) United States Patent
Flath et al.

(10) Patent No.: US 10,441,547 B2
(45) Date of Patent: Oct. 15, 2019

(54) TAMPER RESISTANT CO-EXTRUDED DOSAGE FORM CONTAINING AN ACTIVE AGENT AND AN ADVERSE AGENT AND PROCESS OF MAKING SAME

(71) Applicant: Purdue Pharma L.P., Stamford, CT (US)

(72) Inventors: Robert P. Flath, Yonkers, NY (US); John K. Masselink, Old Tappan, NJ (US)

(73) Assignee: PURDUE PHARMA L.P., Stamford, CT (US)

( * ) Notice: Subject to any disclaimer, the term of this patent is extended or adjusted under 35 U.S.C. 154(b) by 34 days.

(21) Appl. No.: 14/513,585

(22) Filed: Oct. 14, 2014

(65) Prior Publication Data

US 2015/0140086 A1 May 21, 2015

Related U.S. Application Data

(60) Continuation of application No. 12/236,063, filed on Sep. 23, 2008, now Pat. No. 8,883,204, which is a division of application No. 10/582,256, filed as application No. PCT/US2004/041154 on Dec. 8, 2004, now abandoned.

(60) Provisional application No. 60/528,550, filed on Dec. 9, 2003.

(51) Int. Cl.
| | |
|---|---|
| *A61K 9/24* | (2006.01) |
| *A61K 31/44* | (2006.01) |
| *A61K 9/50* | (2006.01) |
| *A61K 9/16* | (2006.01) |
| *A61K 31/135* | (2006.01) |
| *A61K 31/137* | (2006.01) |
| *A61K 31/439* | (2006.01) |
| *A61K 31/485* | (2006.01) |

(52) U.S. Cl.
CPC ............ *A61K 9/5073* (2013.01); *A61K 9/167* (2013.01); *A61K 9/1694* (2013.01); *A61K 9/5026* (2013.01); *A61K 9/5047* (2013.01); *A61K 31/135* (2013.01); *A61K 31/137* (2013.01); *A61K 31/439* (2013.01); *A61K 31/485* (2013.01)

(58) Field of Classification Search
CPC ............................ A61K 31/485; A61K 9/5084
See application file for complete search history.

(56) References Cited

U.S. PATENT DOCUMENTS

| | | |
|---|---|---|
| 3,493,657 A | 2/1970 | Lewenstein et al. |
| 3,773,955 A | 11/1973 | Pachter et al. |
| 3,966,940 A | 6/1976 | Pachter et al. |
| 4,457,933 A | 7/1984 | Gordon et al. |
| 4,582,835 A | 4/1986 | Lewis et al. |
| 4,880,585 A | 11/1989 | Klimesch et al. |
| 4,957,681 A | 9/1990 | Klimesch et al. |
| 5,073,379 A | 12/1991 | Klimesch et al. |
| 5,266,331 A | 11/1993 | Oshlack et al. |
| 5,324,351 A | 6/1994 | Oshlack et al. |
| 5,334,392 A | 8/1994 | Cuine et al. |
| 5,356,467 A | 10/1994 | Oshlack et al. |
| 5,451,409 A | 9/1995 | Rencher et al. |
| 5,462,747 A | 10/1995 | Radebaugh et al. |
| 5,472,712 A | 12/1995 | Oshlack et al. |
| 5,492,692 A | 2/1996 | Digenis et al. |
| 5,500,227 A * | 3/1996 | Oshlack ............... A61K 9/2866 424/468 |
| 5,508,042 A | 4/1996 | Oshlack et al. |
| 5,549,912 A | 8/1996 | Oshlack et al. |
| 5,639,476 A | 6/1997 | Oshlack et al. |
| 5,656,295 A | 8/1997 | Oshlack et al. |
| 5,935,975 A | 8/1999 | Rose et al. |
| 5,958,452 A | 9/1999 | Oshlack et al. |
| 5,965,161 A | 10/1999 | Oshlack et al. |
| 5,968,551 A | 10/1999 | Oshlack et al. |
| 6,063,405 A | 5/2000 | Drizen et al. |
| 6,120,802 A | 9/2000 | Breitenbach et al. |
| 6,143,328 A | 11/2000 | Heafield et al. |
| 6,190,591 B1 | 2/2001 | van Lengerich |
| 6,194,000 B1 | 2/2001 | Smith et al. |
| 6,228,863 B1 | 5/2001 | Palermo et al. |
| 6,294,195 B1 | 9/2001 | Oshlack et al. |
| 6,306,391 B1 | 10/2001 | Modi et al. |
| 6,335,033 B2 | 1/2002 | Oshlack et al. |
| 6,696,088 B2 | 2/2004 | Oshlack et al. |
| 7,144,587 B2 | 12/2006 | Oshlack et al. |
| 7,815,934 B2 | 10/2010 | Boehm |
| 2002/0010127 A1* | 1/2002 | Oshlack ............... A61K 9/0031 424/449 |
| 2003/0004177 A1 | 1/2003 | Kao et al. |
| 2003/0096791 A1* | 5/2003 | Gupte .................. A61K 9/5078 514/57 |
| 2003/0124185 A1 | 7/2003 | Oshlack et al. |
| 2003/0143269 A1 | 7/2003 | Oshlack et al. |

(Continued)

FOREIGN PATENT DOCUMENTS

| | | |
|---|---|---|
| WO | WO 2004/026283 | 4/2004 |
| WO | WO 2004/093819 | 11/2004 |

OTHER PUBLICATIONS

Gandhi et al., *PSST* 2(4): 160-170 (1999).
Osol, A (ed.) Remington's Pharmaceutical Sciences (1980) pp. 1553-1593.
Remington's Pharmaceutical Sciences 18th ed. (1990) pp. 1684-1685.

(Continued)

*Primary Examiner* — Kyle A Purdy
(74) *Attorney, Agent, or Firm* — Lowenstein Sandler LLP

(57) ABSTRACT

The present invention relates to co-extruded pharmaceutical compositions and dosage forms including an active agent, such as an opioid agonist, and an adverse agent, such as an opioid antagonist. Such compositions and dosage forms are useful for preventing or discouraging tampering, abuse, misuse or diversion of a dosage form containing an active pharmaceutical agent, such as an opioid. The present invention also relates to methods of treating a patient with such a dosage form, as well as kits containing such a dosage form with instructions for using the dosage form to treat a patient.

17 Claims, 2 Drawing Sheets

(56) References Cited

U.S. PATENT DOCUMENTS

2003/0157168 A1 8/2003 Breder et al.
2003/0190362 A1 10/2003 Sackler et al.
2003/0203055 A1* 10/2003 Rao ..................... A61K 31/00
424/738
2004/0228924 A1 11/2004 Oshlack et al.

OTHER PUBLICATIONS

International Preliminary Report on Patentability for PCT/US2004/041154, dated Jun. 12, 2006, 7 pages.
International Search Report for PCT/US2004/041154, dated May 31, 2005, 6 pages.
Written Opinion of the International Searching Authority for PCT/US2004/041154, dated May 31, 2005, 6 pages.

* cited by examiner

TAMPER RESISTANT CO-EXTRUDED DOSAGE FORM CONTAINING AN ACTIVE AGENT AND AN ADVERSE AGENT AND PROCESS OF MAKING SAME

1. FIELD OF THE INVENTION

The present invention relates to co-extruded pharmaceutical compositions and dosage forms including an active agent, such as an opioid agonist, and an adverse agent, such as an opioid antagonist, which are useful for preventing or discouraging tampering, abuse, misuse or diversion of the dosage form. The present invention also relates to methods of treating a patient with such a dosage form, as well as kits containing such a dosage form with instructions for using the dosage form to treat a patient. The present invention further relates to a co-extrusion process for the preparation of such pharmaceutical compositions and dosage forms.

2. BACKGROUND OF THE INVENTION

There have been previous attempts in the art to increase the tamper resistance of dosage forms, such as opioid analgesic dosage forms. Prior approaches to developing tamper resistant opioid dosage forms have included combining an opioid agonist with an opioid antagonist. Particular examples of such combinations include compositions including naloxone and morphine or oxymorphone (U.S. Pat. No. 3,493,657 to Lewenstein et al.); methadone and naloxone (U.S. Pat. No. 3,773,955 to Pachter et al.); methadol or acetyl methadol and naloxone (U.S. Pat. No. 3,966,940 to Pachter et al.); oxycodone and naloxone (U.S. Pat. No. 4,457,933 to Gordon et al.); and buprenorphine and naloxone (U.S. Pat. No. 4,582,835 to Lewis et al.).

U.S. Pat. No. 6,228,863 to Palermo et al. discloses an oral dosage form which combines an opioid agonist and an opioid antagonist such that at least two separation steps are required to isolate the agonist.

U.S. Pat. No. 5,935,975 to Rose et al. discloses methods for treating drug dependency by the combined administration of the drug, i.e. the agonist, and an antagonist of the drug.

U.S. Patent Application Publication No. 2003/0143269 A1 to Oshlack et al. discloses a dosage form comprising an opioid against in releasable form and a sequestered opioid antagonist which is not substantially released following administration of the intact dosage form.

In addition, it is known in the pharmaceutical art to prepare oral dosage forms which provide for controlled release of therapeutically active agents. Such controlled release compositions are used to delay absorption of at least a portion of the dose of the agent until it has reached certain portions of the gastrointestinal tract. Such controlled release of the agent serves to maintain a desired concentration of the agent in the blood stream for a longer duration than would occur if conventional immediate or rapid release dosage forms were to be administered.

Over the years, several different methods of preparing controlled release pharmaceutical dosage forms have been suggested, including, for example, extrusion, granulation, coating beads and the like.

There remains a need in the art for improved tamper resistant dosage forms and improved techniques for their preparation.

3. SUMMARY OF THE INVENTION

The present invention relates to co-extruded pharmaceutical compositions and dosage forms including an active agent and an adverse agent, and to co-extrusion methods of making such compositions and dosage forms. The present invention also relates to methods of treating a patient with such pharmaceutical compositions or dosage forms, as well as kits including such pharmaceutical compositions or dosage forms and instructions directing the usage of the composition or dosage form to treat a patient. The dosage forms in accordance with the present invention include oral dosage forms, including but not limited to, capsules or tablets, rectal suppositories and vaginal suppositories. The dosage forms comprise co-extruded compositions, including but not limited to one or more particles such as melt-extruded multiparticulates ("MEMs") made by a process comprising co-extrusion.

In one embodiment, the present invention relates to a co-extruded dosage form including a core comprising an adverse agent, and one or more shell layers or components comprising an active agent. In this embodiment, the shell layers or components at least partially surround the core, and preferably, surround a majority of the core. The dosage form is made by a process which comprises co-extrusion of the core and the shell.

In another embodiment, the invention relates to a co-extruded dosage form including a core, a sheath comprising one or more sheath layers or components, and a shell comprising or more shell layers or components. The dosage form is made by a process which comprises co-extrusion of the core, the sheath and the shell. In this embodiment, the core comprises an adverse agent, the sheath comprises a hydrophobic material and at least partially surrounds the core, and the shell comprises an active agent at least partially surrounds the sheath.

Advantageously, in one embodiment, the shell can provide a controlled release of the active agent upon administration to a patient. Also, in one embodiment, the sheath component can contribute to delaying and/or reducing the in vivo release of adverse agent contained in the core.

In one embodiment, the invention is directed to a method of making a tamper-resistant dosage form comprising a) forming a multilayer extrudate by co-extruding a core comprising an adverse agent and a shell comprising an active agent which at least partially surrounds the sheath; and b) rendering the mutlilayer extrudate to form at least one particle. In one embodiment, a rolling punch is used to render the multilayer extrudate into one or more particles.

In one embodiment, the present invention includes a method of making a tamper-resistant dosage form comprising a) forming a multilayer extrudate by co-extruding a core comprising an adverse agent and a hydrophobic material; a sheath comprising a hydrophobic material which at least partially surrounds the core; and a shell comprising an active agent and a hydrophobic material which at least partially surrounds the sheath; b) using a rolling punch to form one more particles from the multilayer extrudate; and c) incorporating one or more particles into a dosage form.

The compositions and dosage forms of the present invention can provide immediate release or controlled release of the active agent.

In certain embodiments, the adverse agent can be sequestered. The sequestered adverse agent can be present in the core, and in one embodiment, the adverse agent can be present only in the core of the dosage form.

The present invention further relates to methods of treating a patient including administering a dosage form of the invention to the patient. In one embodiment of the invention, the patient is treated for pain.

The present invention also includes a method of reducing abuse, misuse or diversion of a dosage form for treating pain, which method includes administering to a patent in need thereof a dosage form of the invention.

In still another embodiment, the invention relates to a kit for treating a patient, including at least one dosage form of the invention and a set of instructions describing the use of the dosage form to treat the patient. In one embodiment of the invention, the kit is for treating a patient's pain.

The present invention can be understood more fully by reference to the following detailed description and examples, which are intended to exemplify non-limiting embodiments of the invention.

4. BRIEF DESCRIPTION OF THE DRAWINGS

5. DETAILED DESCRIPTION OF THE INVENTION

5.1 Definitions

Figure 1A:
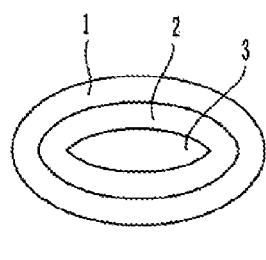
FIGS. 1a, 1b and 1c shows perspective views of embodiments of a dosage form of the present invention.

Any reference herein to any pharmaceutical agent, such as an active agent, an adverse agent, an opioid agonist or an opioid antagonist, shall, unless otherwise stated, include any pharmaceutically acceptable form of such pharmaceutical agent, such as the free form, any pharmaceutically acceptable salt form, any pharmaceutically acceptable base form, any pharmaceutically acceptable hydrate, any pharmaceutically acceptable solvate, any stereoisomer, any optical isomer, as well as any prodrug of such pharmaceutical agent and any pharmaceutically active analog of such pharmaceutical agent, and mixtures of any two or more of the foregoing.

The phrase "pharmaceutically acceptable salt," as used herein, can be a salt formed from an acid and the basic group, such as a nitrogen group, of an active agent or an adverse agent. Generally, examples of such salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, glubionate and palmoate (i.e., 1,1'-methylene-bis-(2-hydroxy-3-naphthoate)) salts. The term "pharmaceutically acceptable salt" can alternatively be a salt prepared from an active agent or an adverse agent having an acidic functional group, such as a carboxylic acid or sulfonic acid functional group, and a pharmaceutically acceptable inorganic or organic base. Generally, examples of such bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methylamine, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

A "patient" or an "animal" is preferably a mammal, and includes, but is not limited to, a cow, monkey, horse, sheep, pig, chicken, turkey, quail, cat, dog, mouse, rat, rabbit, and guinea pig, and most preferably a human.

As used herein, the phrase "active agent" refers to a pharmaceutical agent that causes a biological effect when absorbed in sufficient amount into the blood stream of a patient.

As used herein, the phrase "adverse agent" refers to a pharmaceutical agent that partially or completely negates or reverses at least one biological effect of an active agent present in the dosage form, e.g. euphoric effect, or produces one or more unpleasant physiological reactions, e.g., vomiting, nausea, diarrhea, bad taste, when absorbed in sufficient amount into the blood stream of a patient or animal.

As used herein, the term "controlled release" refers to the in vivo release of an active agent from a dosage form following administration at a rate which will provide a longer duration of action than a single dose of the immediate release dosage form. For example, a typical immediate release oral dosage form can release the drug, e.g., over a 1 hour interval, as compared to a controlled release oral dosage form which can release the drug, e.g., over a 5 to 24 hour interval.

As used herein, the term "layer" refers to a coating or stratum including, but not limited to, a coating of stratum having a single thickness; a coating or stratum having multiple thicknesses; a coating or stratum having opposing surfaces which are parallel; a coating or stratum having opposing surfaces which are not parallel; a coating or stratum having one or more surfaces which are planar; and a coating or stratum having one or more surfaces which are non-planar.

As used herein, the term "laminate" refers to a structure comprising more than one layer, i.e., a multilayer structure.

As used herein, the phrase "opioid agonist" refers to an active agent which binds, optionally stereospecifically, to any one or more of several subspecies of opioid receptors and produces agonist activity.

As used herein, the phrase "opioid antagonist" refers to an adverse agent that either reduces, delays or reverses at least one biological effect of an opioid agonist, e.g., euphoric effect, when absorbed in sufficient amount into the blood stream of a patient or animal.

5.2 Co-Extruded Dosage Forms Including an Active Agent and an Adverse Agent

As stated above, the present invention is directed to co-extruded pharmaceutical compositions and dosage forms including an active agent and an adverse agent, and to co-extrusion methods of making such compositions and dosage forms. In one embodiment, the invention relates to dosage forms including one or more co-extruded particles comprising an active agent and an adverse agent.

The compositions and dosage forms of the invention can provide immediate release or controlled release of the active agent.

In certain embodiments, the adverse agent is not sequestered. In those embodiments, the adverse agent can be released in vivo at any rate, including immediate release and controlled release.

In certain embodiments, the adverse agent is sequestered. In those embodiments, the compositions and dosage forms of the invention are formulated or made in a manner which greatly reduces or prevents the in vivo release or absorption of the sequestered adverse agent into the blood stream following administration as intended of the intact dosage form to a patient. Thus, only a small amount, preferably less than about 10% by weight and more preferably less than about 1% by weight or none, of the sequestered adverse agent present in the dosage form is released in vivo or absorbed into the blood stream following the administration as intended of an intact dosage from to a patient. When the sequestered adverse agent is an opioid antagonist, in certain embodiments, preferably less than about 0.5 mg, and more preferably less than about 0.05 mg, of the opioid antagonist is released in vivo following administration as intended of the intact dosage form to a patient. For example, in one embodiment, when the sequestered adverse agent is naltrexone, preferably less than 0.0625 mg of naltrexone is released in vivo following administration as intended of the intact dosage form to a patient.

In one embodiment, the adverse agent can be sequestered by extruding the adverse agent with at least one hydrophobic material and, optionally, binders, plasticizers, processing aids, excipients, or the like, or combinations of two or more of the foregoing. U.S. Patent Application Publication No. 2003/0143269 A1, which is expressly incorporated herein in its entirety for all purposes, discloses compositions and methods for formulating a dosage form comprising a sequestered adverse agent and an active agent. In one embodiment, the dosage form comprises a sequestered adverse agent present within a core which is at least partially covered or surrounded by one or more sheath layers or components, and the sheath components are at least partially surrounded by one or more shell layers or components comprising an active agent. The dosage form is produced by a process which comprises a co-extrusion of the core, the sheath component(s) and the shell component(s). In one embodiment, the core is at least partially surrounded or covered by the sheath, and a portion of the adverse agent-containing core can be exposed. The sheath can comprise two sheath layers or components that cover or surround at least a portion of, preferably a majority, of the core. In one embodiment, the sheath covers or surrounds a majority of the top and bottom of the core, while leaving some or all of the sides of the core uncovered. In one embodiment, the sheath covers or surrounds substantially all of the top, the bottom and the sides of the core.

In one embodiment, the sheath is at least partially surrounded or covered by the shell, and preferably a majority of the sheath is surrounded or covered by the shell. The shell can comprise two shell layers or components. In one embodiment, the shell covers or surrounds a majority of the top and bottom of the sheath, while leaving some or all of the peripheral surface or sides of the sheath uncovered. In one embodiment, the shell covers or surrounds substantially all of the top, the bottom and the sides of the sheath.

In certain embodiments, the sheath does not cover or surround all of the core. In those embodiments, a portion of the shell can be adjacent to and cover or surround some or all of the portion of the core which is not covered or surrounded by the sheath.

In one embodiment, the present invention relates to solid dosage forms including a plurality of co-extruded particles including an active agent and an adverse agent, wherein the particles comprise a core containing the adverse agent and the core is at least partially surrounded by a shell comprising the active agent. The particles are made by a process comprising co-extrusion of the core and the shell. Preferably, the shell surrounds a majority of the core component. The core can include an adverse agent and a hydrophobic material, and the shell can include an active agent and a hydrophobic material. In one embodiment, the adverse agent is sequestered.

In certain embodiments, the adverse agent can be present throughout the core. In one embodiment, the adverse agent can be present in both the core and the sheath. In another embodiment, the adverse agent can be present in one or more inner layers of a multilayer particle.

In certain embodiments, the sheath does not include any adverse agent or active agent. In other embodiments, the sheath can include an adverse agent and/or an active agent. In one embodiment, the amount of adverse agent present in the sheath is less than the amount present in the core. Similarly, in one embodiment, the amount of active agent present in the sheath is less than the amount present in the shell.

In certain embodiments, the shell does not include any adverse agent. In other embodiments, the shell can include an adverse agent. In one embodiment, the amount of adverse agent present in the shell is less than the amount of adverse agent present in the core. If present, the adverse agent included in the shell can be immediate release or controlled release, or can be sequestered.

In one embodiment, the adverse agent is present only in the core, the active agent is present only in the shell, and there is no adverse agent or active agent present in the sheath of the dosage form as co-extruded. In this embodiment, it is acceptable for small amounts of active agent and/or adverse agent to migrate to other components or layers following co-extrusion.

The dosage forms of the invention can be administered orally, such as in the form of a tablet or capsule; or rectally or vaginally, such as in the form of a suppository. In a preferred embodiment, the invention is directed to oral dosage forms.

The dosage forms of the invention can comprise one or more co-extruded particles of any appropriate size. In one embodiment, the dosage form can comprise a plurality of small particles, such as, for example, particles having a size of from about 0.1 mm to about 5.0 mm in all dimensions. In another embodiment, the particles have a dimension of from about 0.1 mm to about 3.0 mm in all dimensions. The particles can have any shape, such as cylindrical, spherical, square, ellipsoid, or any regular or irregular form, as desired.

In one embodiment, an oral dosage form is prepared to include an effective amount of melt-extruded multiparticulates ("MEMs") within a hard or soft gelatin capsule. For example, a plurality of MEMs containing a core, a sheath and a shell can be placed in a gelatin capsule in an amount sufficient to provide an effective sustained-release dose of the active agent when ingested and contacted by body fluid, without significant release of the sequestered adverse agent. The particle size of the multiparticulates of the dosage form of the invention is from about 0.1 mm to about 5.0 mm in all dimensions; in another embodiment, from about 0.1 mm to about 3.0 mm in all dimensions.

In another embodiment, a plurality of particles or MEMs can be compressed into tablets, for example, by the procedures set forth in U.S. Pat. No. 4,957,681 (Klimesch, et al.), which is expressly incorporated herein by reference in its entirety for all purposes. Techniques and compositions for making tablets (compressed and molded), capsules (hard and soft gelatin) and other forms of pills are also described in *Remington's Pharmaceutical Sciences* (Arthur Osol, editor), 1553-1593 (1980), incorporated by reference herein in its entirety for all purposes.

Figure 2:
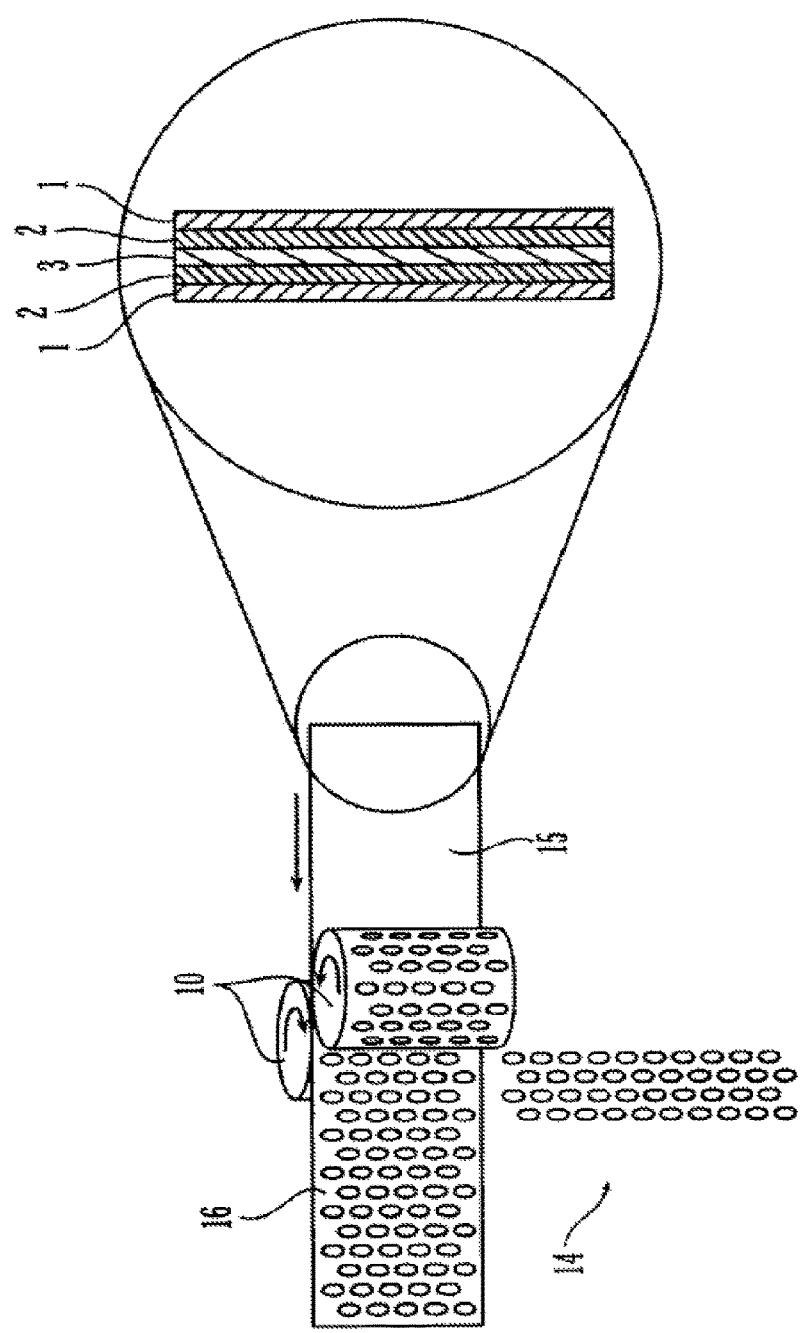
FIG. 2 illustrates one embodiment of the invention in which particulates of the invention are prepared from a multi-layer sheet using a rolling punch.

In another embodiment, a tablet can be prepared by forming a co-extruded extrudate into tablets using devices such as a molding roll, a pinch device, a belt and a roller or tow rollers. In another embodiment, a tablet can be prepared from an extrudate sheet using a rolling punch, as shown in FIG. 2.

It is to be understood that the tablets can be any geometrical shape such as, for example, spherical, oval, pellet, etc., and can vary in size in any dimension depending on the method of manufacture and the patient. The tablet can have a dimension in any direction from about 5 mm to about 75 mm. In one embodiment, the tablet has a dimension in any direction from about 5 mm to about 30 mm. In another embodiment, the tablet has a dimension in any direction from about 5 mm to about 15 mm.

The particles or tablets of the invention can further comprise pharmaceutically acceptable hydrophobic coating materials as defined above in Section 5.5; excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); wetting agents (e.g., sodium lauryl sulphate); and other additives or excipients or as is well-known in the art. The particles or tablets can be coated by methods well-known in the art provided such coating does not interfere with the intended use. Non-limiting examples of coating processes are spray coating and dip coating.

In certain embodiments, the dosage forms are formulated to provide controlled release of the active agent in vivo, e.g., over about 5 to 8 hours or longer, preferably over at least 12 hours, more preferably over at least 24 hours, or longer.

While it is contemplated by the inventors that, for certain purposes, the release rate of the active agent and the adverse agent can be measured by in vivo methods or in vitro methods, the inventors do not represent that there is a direct correlation between the results obtained via the two different methods.

When administered as intended to a patient, the in vivo release of any adverse agent from the intact dosage form will preferably be sufficiently low so that it will not substantially reduce the benefits of the active agent or produce any unpleasant physiological reaction. The release rate of the adverse agent will be determined in large part by the composition of the core, the sheath and the shell. The dosage form of the invention will typically release less than about 10% by weight of, preferably less than about 1% by weight of, more preferably substantially no sequestered adverse agent in vivo following administration as intended of the intact dosage form. When the sequestered adverse agent is an opioid antagonist, the dosage form will preferably release less than about 0.5 mg, more preferably less than about 0.05 mg, of the opioid antagonist in vivo following administration as intended of the intact dosage form. For example, in one embodiment, when the adverse agent is naltrexone opioid antagonist, preferably less than 0.0625 mg of naltrexone is released in vivo following administration of the intact dosage form as intended.

In certain embodiments, the dosage form preferably releases less than about 10% by weight, more preferably less than about 1% by weight, more preferably substantially no adverse agent over a 36 hour period during a standard in vitro dissolution test. For example, when the oral dosage form contains 5.0 mg of sequestered opioid antagonist and a dissolution test is conducted using the USP Basket Method (USP Type I basket, 100 rpm; 700 ml simulated gastric filled, pH 1.2 without enzyme; 37° C. for 1 hour followed by 900 ml simulated intestinal fluid; pH 7.5 without enzyme for the duration of the test), the quantity of opioid antagonist released in simulated gastrointestinal fluid over 36 hours can be less than 0.5 mg, and more preferably less than 0.05 mg.

When an intact dosage form including an active agent and a sequestered adverse agent is administered to a patient, only a small amount, and preferably almost none, of the sequestered adverse agent is released in vivo, whereas the active agent is released at the intended rate, which can vary from immediate release to controlled release. However, when a dosage form including an active agent and a sequestered adverse agent particles is tampered with, e.g., chewed, crushed, ground or dissolved, particularly in a solvent with heat (e.g., greater than from about 45° C. to about 50° C., up to about 100° C. or above), then the amount of adverse agent available for absorption into the body is substantially increased. The adverse agent is then available to exert its effect by either reducing at least one effect of the active agent, e.g., euphoric effect, or eliciting one or more unpleasant effects in the patient. Thus, where the adverse agent is an antagonist of the active agent, at least one effect of the active agent is preferably substantially diminished, or even eliminated, by the effect of the adverse agent. For example, where the active agent is an opioid agonist and the adverse agent is an opioid antagonist, an increased amount of opioid antagonist will become bioavailable when the dosage form is tampered with, interfering with opioid-receptor binding and reducing the opioid agonist's euphoric effect. Accordingly, only patients who take the dosage form of the present invention as intended as an intact dosage form will experience substantially the full pharmacological effect of the active agent. Where the adverse agent is an emetic agent and the dosage form is tampered with, the release and absorption of the emetic agent will induce nausea and/or vomiting to discourage the user from tampering with the dosage form and also, in certain instances, to remove the active agent from the subject's body. Abuse of the active agent in the dosage form will thus become less desirable because of the undesirable effects caused by the adverse agent.

In one embodiment of the invention, the solid dosage form can optionally be covered by a cosmetic coating. Any known type of cosmetic coating used for pharmaceutical dosage forms can be used so long as the release of the coated dosage form achieves the intended purpose of the invention.

In certain embodiments, the dosage form can be cured by exposure to prolonged elevated temperatures in order to achieve increased stability. As used herein, the term "curing" means the heat treatment of the dosage form (or intermediate product) for purposes of obtaining a stabilized final dosage form. As understood by those skilled in the art, when the formulations of the invention incorporate a polymer as part or all of the hydrophobic retarding agent, a heat treatment causes a curing effect and the polymer possibly cross-links with itself into a more stable state. When the formulations of the invention include a hydrophobic material such as, e.g., hydrogenated vegetable oil or stearyl alcohol, the heat treatment can be more akin to an annealing of the formulation rather than a curing of the polymer. However, for purposes of the present invention, the use of the term "curing" is deemed to encompass both curing and annealing. In situations where the hydrophobic material includes only a wax-like substance, curing can be accomplished at a temperature from about 35° C. to about 65° C., for a time period sufficient to achieve maximum stability, such as for a time period from about 4 to about 72 hours. In other embodiments, curing is conducted at a temperature of from about 40° C. to about 60° C., for a time period from about 5 to about 48 hours or more, and preferably at least about 24 hours. Suitable curing times that achieve the intended result of a stabilized dosage form can be determined by those of skill in the art.

5.3 Active Agent

Any kind of active agent can be used in the co-extruded dosage forms of the present invention. Examples of useful active agents include, but are not limited to, analgesics, anti-inflammatory agents, anthelmintics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile-dysfunction-improvement agents, immunosuppressants, anti-protozoal agents, anti-thyroid agents, anxiolytic agents, sedatives, hypnotics, neuroleptics, β-blockers, cardiac ionotropic agents, corticosteroids, diuretics, anti-parkinsonian agents, gastrointestinal agents, histamine receptor antagonists, keratolytics, lipid regulating agents, anti-anginal agents, cox-2-inhibitors, leukotriene inhibitors, macrolides, muscle relaxants, nutritional agents, opioid analgesics, protease inhibitors, sex hormones, stimulants, muscle relaxants, anti-osteoporosis agents, anti-obesity agents, cognition enhancers, anti-urinary incontinence agents, nutritional oils, anti-benign prostate hypertrophy agents, essential fatty acids, and non-essential fatty acids. The dosage forms can comprise more than one active agent.

More specific examples of active agents include, but are not limited to, opioids, benzodiazepines, barbiturates, and stimulants, such as methylphenidate and amphetamines, dronabinol, glutethimide, methylphenidate, nabilone, anabolic steroids, methylprylon, ethchlorovynol, ethinamate, fenfluramine, meprobamate, pemoline, levomethadyl, benzphetamine, chlorphentermine, diethylpropion, phentermine, mebutamate, chlortermine, phenylacetone, dronabinol, nabilone, benphetamine, chloral hydrate, ethclorovynol, paraldehyde, midazolam, and detropropoxyphene.

In certain embodiments, the active agent is an opioid agonist. Useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, etorphine, dihydroetorphine, fentanyl, hydrocodone, hydromorphone, hydromorphodone, hydroxypethidine, isomethadone, ketobemidone, levorphanol, levophenacylmorphan, lofentanil, meperidine, meptazinol, metazocine, methadone, metopon, morphine, myrophine, narceine, nicomorphine, norlevorphanol, normethadone, nalorphine, nalbuphene, normorphine, norpipanone, opium, oxycodone, oxymorphone, pantopon, papaveretum, paregoric, pentazocine, phenadoxone, phendimetrazine, phendimetrazone, phenomorphan, phenazocine, phenoperidine, piminodine, piritramide, propheptazine, promedol, properidine, propoxyphene, propylhexedrine, sufentanil, tilidine, tramadol, pharmaceutically acceptable salts thereof, and mixtures of any two or more of the foregoing.

In certain embodiments, the opioid agonist is selected from the group consisting of hydrocodone, morphine, hydromorphone, oxycodone, codeine, levorphanol, meperidine, methadone, oxymorphone, buprenorphine, fentanyl and derivatives thereof, dipipanone, heroin, tramadol, etorphine, dihydroetorphine, butorphanol, levorphanol and mixtures thereof. In one embodiment, the opioid agonist is oxycodone, hydromorphone or hydrocodone.

The term "benzodiazepines" refers to benzodiazepine and drugs that are derivatives of benzodiazepine and are able to depress the central nervous system. Benzodiazepines include, but are not limited to, alprazolam, bromazepam, chlordiazepoxied, clorazepate, diazepam, estazolam, flurazepam, halazepam, ketazolam, lorazepam, nitrazepam, oxazepam, prazepam, quazepam, temazepam, triazolam, methylphenidate and mixtures of any two or more of the foregoing.

Barbiturates refer to sedative-hypnotic drugs derived from barbituric acid (2,4,6, -trioxohexahydropyrimidine). Barbiturates include, but are not limited to, amobarbital, aprobarbotal, butabarbital, butalbital, methohexital, mephobarbital, metharbital, pentobarbital, phenobarbital, secobarbital and mixtures of any two or more of the foregoing.

Stimulants refer to drugs that stimulate the central nervous system. Stimulants include, but are not limited to, amphetamines, such as amphetamine, dextroamphetamine resin complex, dextroamphetamine, methamphetamine, methylphenidate and mixtures of any two or more of the foregoing.

The active agent can be an agent intended for delivery to the colon, including, but not limited to, agents that act locally in the colonic region to treat a colon diseases such as irritable bowel syndrome, irritable bowel disease, Crohns disease, constipation, post operative atony, gastrointestinal infections, and therapeutic agents that deliver antigenic material to the lymphoid tissue. Active agents for the treatment of colon disease include, but are not limited to 5-ASA; steroids, such as hydrocortisone and budesonide; laxatives; stool softeners; octreotide; cisapride; anticholinergics; opioids; calcium channel blockers; DNA for delivery to the cells of the colon; glucosamine; thromboxane $A_2$ synthetase inhibitors, such as Ridogrel; 5HT3-antagonists, such as ondansetron; antibodies against infectious bacteria, such as *Clostridium difficile*; and antiviral agents, for example, for the prophylaxis of HIV.

Alternatively, the active agent can be an agent that is systemically active and for which absorption is improved in the colon region. Such drugs include polar compounds such as: heparins; insulin; calcitonins; human growth hormone (HGH); growth hormone releasing hormone (GHRH); interferons; somatostatin and analogues such as octreotide and vapreotide; erythropoietin (EPO); granulocyte colony stimulating factor (GCSF); parathyroid hormone (PTH); luteinising hormone releasing hormone (LHRH) and analogues thereof; atrial natriuretic factor (ANF); vasopressin; desmopressin; calcitonin gene related peptide (CGRP); and analgesics.

The active agent particles can further comprise hydrophobic materials, binders, plasticizers, excipients, and combinations of any two or more of the foregoing. Suitable matrix materials include those which allow release of the active agent at a rate sufficient to achieve the desired result, e.g., immediate release or sustained release. In one embodiment, permeable matrix material is used, allowing for diffusive release of the active agent into the gastrointestinal fluid.

5.4 Adverse Agent

As noted above, the present invention is directed to co-extruded dosage forms and pharmaceutical compositions including an active agent and an adverse agent, which can be sequestered, as well as co-extrusion methods for making and administering such dosage forms and compositions. In one embodiment, the invention relates to dosage forms including a plurality of particles including a an active agent and an adverse agent, which can be sequestered.

The adverse agent can be any pharmaceutical active agent which at least partially reduces or blocks the biological effect of an active agent or which creates an unpleasant effect when absorbed into an animal's or patient's blood stream. Examples of adverse agents include, but are not limited to, antagonists of any therapeutically active agonist. When an opioid agonist is used as the active agent in the dosage form of the present invention, an opioid antagonist can be used as the adverse agent. Likewise, when a benzodiazepine is used as the active agent in the dosage form of the present invention, a benzodiazepine antagonist can be used as the adverse agent. When a barbiturate is used as an active agent in the dosage form of the present invention, a barbiturate antagonist can be used as the adverse agent. When an amphetamine is used as an active agent in the dosage form of the present invention, an amphetamine antagonist can be used as the adverse agent. When the active agent is toxic when dosed above its normal therapeutic range, i.e., when there is a significant potential for an overdose, then an antidote of the toxic active agent can be used as the adverse agent.

In one embodiment, the adverse agent is an opioid antagonist. Opioid antagonists useful in the present invention include, but are not limited to, naloxone, naltrexone, nalmefene, nalbuphine, nalorphine, cyclazacine, cyclazocine, levallorphan, pharmaceutically acceptable salts thereof, and mixtures of any two or more of the foregoing.

Useful opioid antagonist salts include salts formed from an acid and the basic nitrogen group of an opioid antagonist. Examples of opioid antagonist salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and palmoate (i.e., 1,1'-methylene-bis-(2-hydroxy-3-naphthoate)) salts.

Other opioid antagonist salts include salts prepared from an antagonist having an acidic functional group, such as a carboxylic acid or sulfonic acid functional group, and a pharmaceutically acceptable inorganic or organic base. Suitable bases include, but are not limited to those identified above in Section 5.1 in the paragraph which references the term "pharmaceutically acceptable salt".

In certain embodiments, the opioid antagonist is nalmefene, naloxone, naltrexone, or a pharmaceutically acceptable salt thereof. In another embodiment, the opioid antagonist is a naltrexone salt, such as naltrexone hydrochloride.

Benzodiazepine antagonists that can be used as the adverse agent of the present invention include, but are not limited to, flumazenil.

Barbiturate antagonists which can be used as the adverse agent of the present invention include, but are not limited to, amphetamines, as described herein.

Stimulant antagonists that can be used as the adverse agent of the present invention include, but are not limited to, benzodiazepines, described herein.

In another embodiment of the present invention, the adverse agent is an agent that causes an undesired physiological reaction, such as emesis. This type of adverse agent can be used with any kind of therapeutic agent including an opioid, a benzodiazepine, a barbiturate, or a stimulant. Examples of emetic agents suitable for use as the adverse agent in the present invention includes any drug that safely and effectively induces vomiting after administration including, but not limited to, ipecac and apomorphine.

5.5 Core

In certain embodiments the present invention, the adverse agent, which can be sequestered, can be present in the core or in an inner layer of a co-extruded, multi-layer particle. In one embodiment, the adverse agent-containing core of the present invention preferably includes a hydrophobic matrix material. Hydrophobic matrix materials useful in the present invention include those that are known in the art to be insoluble or to have a low solubility in the gastrointestinal tract. Such materials include, but are not limited to, a hydrophobic material selected from the group consisting of acrylic and methacrylic acid polymers and copolymers, and alkylcelluloses. The matrix can also include additional hydrophobic materials such as zein, shellac, hydrogenated castor oil, hydrogenated vegetable oil or mixtures thereof. Although insoluble, such hydrophobic materials can degrade over time, thereby eventually releasing some portion of the adverse agent. One of ordinary skill in the pharmaceutical arts can control the rate of such release by, for example, altering the content of the hydrophobic matrix material in the adverse agent core in order to alter the in vivo release of the adverse agent.

In one embodiment, the hydrophobic matrix material includes acrylic polymers. Examples of suitable acrylic polymers include, but are not limited to acrylic acid and methacrylic acid copolymers, methyl methacrylate copolymers, ethoxyethyl methacrylates, cyanoethyl methacrylates, aminoalkyl methacrylate copolymer, poly(acrylic acid), poly(methacrylic acid), methacrylic acid alkylamide copolymers, poly(methyl methacrylate), polymethacrylate, poly (methyl methacrylate) copolymer, poly(methacrylic acid) (anhydride), methyl methacrylate, polyacrylamide, aminoalkyl methacrylate copolymer, poly(methacrylic acid anhydride), and glycidyl methacrylate copolymers. Additional examples of suitable acrylic polymers include, but are not limited to, acrylic resins including copolymers synthesized from acrylic and methacrylic acid esters (e.g., the copolymer of acrylic acid lower alkyl ester and methacrylic acid lower alkyl ester) containing about 0.02 to 0.03 moles of a tri (lower alkyl) ammonium group per mole of acrylic and methacrylic monomer.

The acrylic polymer can comprise one or more ammonio methacrylate copolymers. Ammonio methacrylate copolymers are well known in the art, and are fully polymerized copolymers of acrylic and methacrylic acid esters with a low content of quaternary ammonium groups. In order to obtain a desirable dissolution profile for a given therapeutic agent, it might be necessary to incorporate two or more ammonio methacrylate copolymers having differing physical properties. For example, it is known that by changing the molar ratio of the quaternary ammonium groups to neutral (meth) acrylic esters, the permeability properties of the resultant coating can be modified. One of ordinary skill in the art will readily be able to combine monomers to provide a copolymer that releases the therapeutic agent at the desired release rate. Copolymers of acrylate and methacrylate having a quaternary ammonium group functionality are commercially available as EUDRAGIT RS™ and EUDRAGIT RL™ (Röhm Pharma, GmbH, Weiterstat, Germany). Preferred ammonio methacrylate resins include EUDRAGIT RS™ in all forms, such as EUDRAGIT RS PO™. EUDRAGIT RS™ is known to be a water-insoluble copolymer of ethyl acrylate (EA), methyl methacrylate (MM) and trimethylammonium ethyl methacrylate chloride (TAM) in which the molar ratio of EA:MM:TAM is 1:2:0.01; see, e.g., U.S. Pat. No. 6,306, 391. EUDRAGIT RS PO™ is known to be a powdered form of EUDRAGIT RS™; see, e.g., U.S. Pat. No. 5,492,692.

In one embodiment the hydrophobic matrix material includes a water insoluble cellulose polymer. In certain embodiments, the cellulose polymer is a cellulose ether, a cellulose ester, or a cellulose ester ether. Preferably, the cellulose polymers have a degree of substitution ("D.S.") on the anhydroglucose unit of from about zero up to and including about 3. As used herein the term D.S. means the average number of hydroxyl groups present on the anhydroglucose unit of the cellulose polymer that are replaced by a substituent group. Representative cellulose polymers include, but are not limited to, polymers selected from cellulose acylate, cellulose diacylate, cellulose triacylate, cellulose acetate, cellulose diacetate, cellulose triacetate, mono-, di-, and tricellulose alkanylates, mono-, di-, and tricellulose aroylates, and mono-, di-, and tricellulose alkenylates. Exemplary cellulose polymers include cellulose acetate having a D.S. of from about 1 to about 2 and cellulose acetate having a D.S. of from about 2 to about 3. Preferably, the cellulose polymer is ethylcellulose, cellulose acetate, cellulose propionate (low, medium, or high molecular weight), cellulose acetate propionate, cellulose acetate butyrate, cellulose acetate phthalate, or cellulose triacetate. A more preferred cellulose is ethylcellulose.

More specific cellulose polymers include cellulose propionate having a D.S. of about 1.8; cellulose acetate butyrate having a D.S. of about 1.8; cellulose triacylate having a D.S. of about 2.9 to 3, such as cellulose triacetate, cellulose trivalerate, cellulose trilaurate, cellulose tripalmitate, cellulose trisuccinate, and cellulose trioctanoate; cellulose diacylates having a D.S. of about 2.2 to 2.6 such as cellulose disuccinate, cellulose dipalmitate, cellulose dioctanoate, cellulose dipentanoate; and coesters of cellulose such as cellulose acetate butyrate, cellulose acetate octanoate butyrate, and cellulose acetate propionate.

In certain embodiments, the core can generally comprise from about 30% to about 99% by weight of one or more hydrophobic matrix materials, preferably from about 50% to about 95% by weight of the one or more hydrophobic matrix materials, more preferably from about 60% to about 95% by weight of the one or more hydrophobic matrix materials.

The adverse agent-containing core can optionally comprise one or more binders, additional retardants, plasticizers, and/or excipients. Binders are useful for maintaining the integrity of the matrix and can also help to delay the release of an agent into the bodily fluid. Examples of binders include natural and synthetic waxes, water insoluble waxes, fatty alcohols, fatty acids, hydrogenated fats, fatty acid esters, fatty acid glyercides, hydrocarbons, and hydrophobic and hydrophilic polymers having hydrocarbon backbones, and mixtures such as, stearyl alcohol, stearic acid, and water soluble polymers such as hydroxycelluloses.

Plasticizers are useful when the hydrophobic matrix material contains cellulose polymer or an acrylic polymer. Non-limiting examples of suitable plasticizers include, e.g., acetyl triethyl citrate and/or acetyl tributyl citrate.

The adverse agent core can also include other excipients, which can be added to improve the processability of the formulation during extrusion and/or to improve the properties of the final product. Non-limiting examples of liquid excipients include water and oils, including those of petroleum, animal, vegetable, or synthetic origin, such as peanut oil, soybean oil, mineral oil, sesame oil, castor oil, triglycerides and the like. Examples of solid excipients include magnesium stearate, saline, gum acacia, gelatin, starch paste, talc, keratin, colloidal silica, urea and the like. Coloring agents can also be added to the core.

In certain embodiments, the core can comprise one or more of the materials disclosed in Section 5.7 with respect to the shell of the dosage form of the present invention.

5.6 Sheath

In certain embodiments, the dosage form of the present invention can include a sheath which at least partially surrounds the adverse agent-containing core, and preferably surrounds a majority of the adverse agent-containing core. In certain embodiments, the sheath preferably includes a hydrophobic matrix material and, optionally, binders, additional retardants, plasticizers and excipients. While, in certain embodiments, the sheath can contain adverse agent and/or active agent, it is preferred that the sheath does not contain any adverse agent or active agent.

In one embodiment, the hydrophobic material of the sheath includes one or more materials selected from the group consisting of acrylic and methacrylic acid polymers and copolymers, and water insoluble alkylcelluloses as described above for the core. The sheath can optionally comprise one or more additional hydrophobic materials, such as shellac, zein, hydrogenated castor oil, hydrogenated vegetable oil and mixtures thereof, as described above for the core.

The hydrophobic matrix material used in the sheath can be the same as or different from that used in the adverse agent core. Although the hydrophobic material used in the sheath will preferably be substantially insoluble in the gastrointestinal tract, this material could dissolve or biodegrade in vivo to some limited extent over time, thereby permitting the in vivo release from the core of a small amount of sequestered adverse agent. One of ordinary skill in the pharmaceutical arts can alter the rate of such release, for example, by altering the composition of the sheath, increasing the thickness of the sheath, surrounding a larger portion of the core with the sheath, varying the size and/or dimensions of the core and/or varying the composition of the sheath and/or core. These and other methods will be known to one of ordinary skill in the art or can be determined by routine experimentation in view of this disclosure.

In certain embodiments, the sheath can comprise from about 10% to about 99% by weight, preferably from about 40% to about 95% by weight, and more preferably from about 60% to about 90% by weight of the one or more hydrophobic matrix materials.

The sheath can further comprise one or more additional retardants or one or more binders or plasticizers or excipients, or any combination thereof, such as those described above for the adverse agent-containing core.

5.7 Shell

The co-extruded dosage form of the present invention includes a shell comprising an active agent. The dosage form can provide immediate release and/or controlled release of the active agent in vivo following administration. In certain embodiments, the dosage form provides a controlled release of the active agent, such as an opioid agonist. Formulations and extrusion methods of manufacture of controlled release dosage forms of opioid agonists are known in the art. For example, U.S. Pat. Nos. 5,958,452; 5,965,161; 5,968,551; 6,294,195 and 6,335,033, each of which is expressly incorporated herein by reference in its entirety for all purposes, disclose controlled release opioid agonist dosage forms. The disclosure of one or more of such patents includes details such as formulations, hydrophobic matrix materials, retardants, binders, plasticizers, and excipients, as well as extrusion methods for forming tablets, caplets and capsules containing MEMs, for controlled release opioid agonist dosage forms.

In certain embodiments, the active agent can be dispersed in a matrix which provides controlled release of the active agent in vivo following oral administration. Any suitable controlled-release matrix can be used to make the pharmaceutical compositions or dosage forms. Certain controlled-release matrices are known for oral formulations (See, e.g., *Remington's Pharmaceutical Sciences* 1684-85 (18th ed. 1990), the disclosure of which is expressly incorporated herein in its entirety for all purposes). In addition to the controlled release dosage forms disclosed in the above-identified patents and publications, other examples of useful controlled-release matrices are described in U.S. Pat. Nos. 6,143,328; 6,063,405; 5,462,747; 5,451,409; 5,334,392; 5,266,331, 5,549,912, 5,508,042, 5,656,295, 5,324,351, 5,356,467, and 5,472,712, the contents of which are each expressly incorporated herein by reference in its entirety for all purposes.

The controlled-release matrix can include fusible hydrophobic material(s), optionally combined with hydrophilic material(s). The hydrophobic fusible material(s) can be, for example, a hydrophobic polymer or a natural or synthetic wax or oil, such as hydrogenated vegetable oil or hydrogenated castor oil, which can, for example, have a melting point of from about 45° C. to about 100° C., and in one embodiment from about 50° C. to about 90° C. The hydrophilic material can be a hydrophilic polymer such as a hydroxycellulose; a water soluble fusible material, such as polyethylene glycol; or a water soluble particulate material, such as dicalcium phosphate or lactose.

While any known co-extrusion method can be used to make controlled release dosage forms according to the present invention, the preferred method is melt co-extrusion of the ingredients with suitable matrix materials. For example, the shell comprising an active agent dispersed in a controlled-release matrix can be prepared by, e.g., extruding the active agent with a suitable non-fusible material including, but are not limited to, one or more of the following:

(a) Hydrophilic or hydrophobic polymers, such as gums, cellulose ethers, protein-derived materials, nylon, acrylic resins, polylactic acid, polyvinylchloride, starches, polyvinylpyrrolidones, and cellulose acetate phthalate. Of these polymers, cellulose ethers, for example, substituted cellulose ethers such as alkylcelluloses (e.g., ethylcellulose), $C_1$-$C_6$ hydroxyalkylcelluloses (e.g., hydroxypropylcellulose and hydroxyethyl cellulose), and acrylic resins (e.g., methacrylates such as methacrylic acid copolymers) can be used. The controlled-release matrix can conveniently contain from about 1% to about 80% (by weight) of the hydrophobic and/or hydrophilic polymer.

(b) Digestible, long chain ($C_8$-$C_{50}$, in one embodiment $C_8$-$C_{40}$) substituted or unsubstituted hydrocarbons, such as fatty acids; hydrogenated vegetable oils; fatty alcohols, such as lauryl, myristyl, stearyl, cetyl or, in one embodiment cetostearyl alcohol; glyceryl esters of fatty acids, for example, glyceryl monostearate; mineral oils; and waxes, such as beeswax, glycowax, castor wax, and carnauba wax. Hydrocarbons having a melting point of from about 25° C. to about 90° C. are used in one embodiment. Of these long chain hydrocarbon materials, fatty (aliphatic) alcohols are useful in one embodiment. The controlled-release matrix can contain up to about 60% (by weight) of at least one digestible, long chain hydrocarbon.

(c) Polyalkylene glycols. The controlled-release matrix can contain up to about 60% (by weight) of at least one polyalkylene glycol.

A suitable controlled-release matrix for use in the dosage form of the invention can include one or more cellulose ethers or acrylic resins, one or more $C_{12}$-$C_{36}$ aliphatic alcohols, in one embodiment $C_{12}$-$C_{22}$ aliphatic alcohols, and/or one or more hydrogenated vegetable oils. A particular suitable matrix includes one or more alkylcelluloses, one or more $C_{12}$-$C_{36}$ aliphatic alcohols, in one embodiment $C_{12}$-$C_{22}$ aliphatic alcohols, and optionally one or more polyalkylene glycols. In another embodiment, the matrix contains from about 0.5% to about 60% by weight, and in another embodiment from about 1% to about 50% by weight, of the cellulose ether.

The acrylic resin can be, for example, a methacrylate such as methacrylic acid copolymer USNF Type A (EUDRAGIT L™), Type B (EUDRAGIT S™), Type C (EUDRAGIT L 100-55™), EUDRAGIT NE 30 D™, EUDRAGIT E™, EUDRAGIT RL™, or EUDRAGIT RS™ (commercially available from Röhm Pharma GmbH, Weiterstat, Germany). In one embodiment, the matrix contains from about 0.5% to about 95% by weight of acrylic resin, and in another embodiment from about 10% to about 50% by weight of acrylic resin.

In the absence of polyalkylene glycol, the matrix in one embodiment contains from about 1% to about 40% by weight, in another embodiment from about 2% to about 36% by weight of the aliphatic alcohol. When polyalkylene glycol is present in the oral dosage form, then the combined weight of the aliphatic alcohol and the polyalkylene glycol in one embodiment constitutes from about 2% to about 40% by weight, in another embodiment from about 2 to about 36% by weight of the matrix.

The polyalkylene glycol can be, for example, polypropylene glycol or, in one embodiment, polyethylene glycol. The number average molecular weight of the polyalkylene glycol is in one embodiment from about 200 to about 15,000 Daltons, and in another embodiment from about 400 to about 12,000 Daltons.

The shell may also comprise one or more of the materials disclosed for inclusion in the core. For example, the shell may comprise one or more of the hydrophobic matrix materials binders, retardants, plasticizers and/or excipients disclosed supra in Section 5.5.

5.8 Co-Extrusion Process

The present invention also relates to co-extrusion methods for preparing a pharmaceutical composition or dosage form. The invention includes processes which comprise co-extruding, such as melt co-extruding, a core including an adverse agent; optionally a sheath which at least partially surrounds the core; and a shell including an active agent which at least partially surrounds the core, and, if present, the sheath. In certain embodiments, the co-extrusion process produces a multilayer extrudate sheet which is rendered into one or more particles of an appropriate size which are then incorporated into one or more dosage forms, including but not limited to, tablets, caplets, or capsules, each of which may comprise or contain a plurality of particles. In one embodiment, the method comprises using a rolling punch to render the multilayer extrudate into particles or tablets.

Generally, methods of preparing active agent-containing compositions or dosage forms by extrusion are well known. See, for example, U.S. Pat. Nos. 5,958,452, 5,965,161 and 6,335,033, each of which is expressly incorporated herein in its entirety for all purposes, which disclose known methods for extruding and forming pharmaceutical dosage forms, including dosage forms comprising particles. Co-extrusion methods to form dosage forms containing an active agent are also known. See, for example, U.S. Pat. Nos. 4,880,585 and 5,073,379, each of which is expressly incorporated herein in its entirety for all purposes.

It is also known to form moldable co-extruded extrudate into tablets by using devices such as a molding roll, a pinch device, a belt and a roller or tow rollers. See, for example, U.S. Pat. Nos. 6,120,802 and 5,073,379, each of which is expressly incorporated herein in its entirety for all purposes.

In accordance with the present invention, a co-extrusion process is used to make multilayer pharmaceutical compositions or dosage forms including an active agent and an adverse agent, which can be sequestered. In one embodiment, the dosage form is made by a process which comprises co-extruding a core, a shell and, optionally, a sheath, and rendering the extrudate into particles using a rolling punch.

In one embodiment, the invention relates to methods of making a dosage form by: a) co-extruding a core comprising an adverse agent and a shell comprising an active agent which at least partially surrounds the core, preferably which surrounds a majority of the core, more preferably which substantially or completely surrounds the core, to form a multilayer extrudate sheet; and b) forming the multilayer extrudate sheet into dosage forms, such as tablets, caplets or a plurality of particles. In one embodiment, the method comprises the use of a rolling punch to render the multilayer extrudate sheet into particles.

In another embodiment, the invention relates to methods of making a dosage form by: a) co-extruding a core including an adverse agent; a sheath, which at least partially surrounds the core, preferably which surrounds a majority of the core, more preferably which substantially or completely surrounds the core; and a shell including an active agent, which at least partially surrounds the sheath, preferably which surrounds a majority of the sheath, more preferably which substantially or completely surrounds the sheath, to form a multilayer extrudate sheet or laminate; and b) forming the multilayer extrudate sheet into dosage forms, such as tablets, caplets or a plurality of particles. In one embodiment, the method comprises the use of a rolling punch to render the multilayer extrudate sheet into particles.

In one embodiment, the dosage form comprises a plurality of particles comprising a core, optionally a sheath, and a shell which are placed in a capsule, preferably a gelatin capsule.

In one embodiment, the present invention further relates to methods of preparing a dosage form including charging a core formulation including an adverse agent and a hydrophobic matrix material into a first extruder; charging a shell formulation including an active agent and a hydrophobic matrix material into a second extruder; heating and extruding the formulations through a multilayer die to form a multilayer extrudate sheet or laminate including an adverse agent core covered at least partially by the shell comprising the active agent; and rendering the multilayer extrudate sheet into dosage forms, such as tablets, caplets or a plurality of particles. In one embodiment, the method can comprise the use of a rolling punch to render the multiplayer extrudate into one or more particles or dosage forms.

An example of an apparatus useful for one embodiment the present invention includes two powder-feeder hoppers, one for loading the adverse agent core components and one for loading the shell components. The core components can include the adverse agent and the hydrophobic matrix material, and optionally additional materials including, but not limited to, additional retardants, binders, plasticizers, processing agents, and excipients, as described above. The shell components comprise the active agent and the hydrophobic matrix materials, and optionally additional materials including, but not limited to retardants, binders, plasticizers, processing agents, and excipients, as described above. The contents of each hopper are charged to an extruder. The outlet of each extruder is attached to a co-extrusion die orifice (all extruders are connected to the same co-extrusion die) that is sized, dimensioned, and configured to be used in the co-extrusion process, thereby forming a multilayer extrudate sheet or laminate, with the adverse agent in the core and the active agent in the shell. In certain embodiments, the multilayer extrudate sheet is configured such that the shell covers the top and bottom of the core. The multilayer extrudate sheet is then rendered into dosage forms. In one embodiment, the method comprises the use of a rolling punch to render the multilayer extrudate sheet into particles or dosage forms.

In another embodiment, the invention further relates to methods of preparing a dosage form including charging a core formulation including an adverse agent and a hydrophobic matrix material into a first extruder; charging a sheath formulation including a hydrophobic matrix material into a second extruder; and charging a shell formulation including an active agent and a hydrophobic material into a third extruder; heating and extruding the formulations in the first, second and third extruders; co-extruding the formulations through a multilayer die to form a multilayer extrudate sheet or laminate; and rendering the multilayer extrudate sheet into dosage forms or particles including a core comprising an adverse agent; a sheath which at least partially covers the core; and a shell including an active agent that at least partially covers the sheath.

An example of an apparatus useful for this embodiment of the invention includes three powder-feeder hoppers, one for loading the core components, one for loading the sheath components and one for loading the shell components. The core components can include the adverse agent and the hydrophobic matrix material, and optionally additional materials including, but not limited to, additional retardants, binders, plasticizers, processing agents, and excipients, as described above. The sheath components can include a hydrophobic matrix material and additional materials including, but not limited to, additional retardants, binders, plasticizers and excipients as described above. Also, as stated above, the sheath components can include the active agent and/or the adverse agent. The shell components can comprise the active agent and the hydrophobic matrix materials, and optionally additional materials including, but not limited to retardants, binders, plasticizers, processing agents, and excipients, as described above. The contents of each hopper are charged to an extruder. The outlet of each extruder is attached to a co-extrusion die orifice (all extruders are connected to the same co-extrusion die) that is sized, dimensioned, and configured to be used in the co-extrusion of a multilayer sheet or laminate, thereby forming a multilayer extrudate sheet or laminate with the adverse agent in the core; a sheath which at least partially surrounds the core, e.g., at least on the top and bottom of the core; and a shell comprising an active agent that at least partially covers the sheath, e.g., at least on the top and bottom of the sheath. In one embodiment, the method comprises the use of a rolling punch to render the multilayer extrudate sheet into particles or dosage forms.

The specific details of the configurations and settings of the extruders used to co-extrude the compositions and dosage forms are not critical to the present invention. The extruder details set forth herein are exemplary. Each extruder can, for example, be equipped with single or twin screws and heated barrels. Each screw extruder can, independently, be of the (i) counter-rotating (i.e., driven in opposite directions of rotation) non-intermeshing; (ii) co-rotating (i.e., driven in the same direction of rotation) non-intermeshing; (iii) counter-rotating intermeshing; or (iv) co-rotating intermeshing type, or some combination thereof. Each extruder can, independently, have a sole discharge port located at the end of its housing or a radial discharge port. Each screw extruder can, independently, have drive means at each end of the screw or a drive means present at only one end. Each screw extruder can, independently, have a length to diameter, or L/D, ratio of from 5-70, preferably from 20-60. Those in the art are familiar with such apparati, e.g., a Leistritz twin screw extruder having a vacuum attachment, a Leistritz Micro 18/GL 40D twin screw extruder, or a Warner & Pfleiderer model ZSK-30 twin screw extruder.

The temperature of each individually adjustable barrel zone of each extruder is set to the required temperature for a given formulation, and the extruder can be allowed to thermally equilibrate, typically for about 30 minutes. The inside pressure of the twin screw extruder can be maintained from about 600 to about 980 mbar negative.

After a steady state temperature is attained, the contents of each powder-feeder hopper are fed into a separate preheated extruder, thereby forming in each extruder an intimately mixed molten mass typically from about 30° C. to about 200° C. in temperature, preferably from about 50° C. to about 150° C., through heating and mixing, as it is driven through a series of zones by intermeshing screws and kneading elements. Optionally, a vent port can be present in the extruder. If it is desired to add a liquid component, independently of any powdered formulation, to a molten mass, the liquid can be injected into the extruder by any known means, for example, by an injection port supplied by a positive displacement pump, such as a gear pump.

The molten masses exiting each extruder are connected to a co-extrusion die orifice, which is optionally downstream of a combining block and/or a main gate adaptor, then passed through the die orifice(s), thereby forming a multilayer extrudate sheet or laminate including an adverse agent core; an optional sheath at least partially surrounding the core; and a shell at least partially covering the core, or if present, the sheath. Generally, the rotation speed, in rpm, of each extruder is adjusted such that their combined output, at the die orifice exit, is from about 1 to about 20 kg/hr or greater, for example from about 6 to about 8 kg/hr. The rotation speed of each extruder is one of the parameters that can be adjusted so that the output of each extruder yields the desired ratio of the core to the shell and, optionally, the sheath.

The dimensions and/or cross-sectional profile of the die orifice can be adjusted to vary the thickness and shape of the resulting multilayer sheet. For example, the die orifice is not limited to a rectangular cross-sectional profile, but can have a trapezoidal character (i.e., where the width of the top of the extrudate is smaller than width of the bottom of the extrudate, or vice versa); can have some degree of curvature associated with the width and/or thickness of the multilayer sheet or laminate (i.e., top and/or bottom sides can have concave and/or convex curvature, such that the thickness changes across the width of the extrudate; in one embodiment, the die orifice opening has a very oblate oval shape); or can have any combination thereof. For example, an orifice having a circular cross-section can be adjusted to provide a multilayer sheet or laminate having a diameter from about 0.1 mm to about 50 mm, alternately from about 0.5 mm to about 20 mm, for example from about 1 mm to about 10 mm.

The multilayer extrudate sheet or laminate produced from the co-extrusion process is thereafter conveyed away from the die orifice and solidified by methods known to those in the art, for example, using a fan-cooled tunnel or a continuous movable belt upon which the multilayer extrudate sheet congeals, hardens, or cures upon cooling. The multilayer extrudate sheet is directed to a suitable device to render the extruded multilayer extrudate into dosage forms, such as plurality of particles, using a rolling punch device or by any method known in the art. Rendering the multilayer extrudate sheet into dosage forms can occur before, during or after congealing/curing.

In a preferred embodiment, the multilayer extrudate sheet which results from the co-extrusion process is allowed to partially cool and congeal and the multilayer extrudate is then calendared cut by a rolling punch, as shown in FIG. 2. Other methods for forming moldable co-extruded extrudate into tablets or particles by using devices such as a molding roll, a pinch device, a belt and a roller or tow rollers are known (see, for example, U.S. Pat. Nos. 6,120,802 and 5,073,379).

In one embodiment, the co-extruded multilayer extrudate is cut, pinched, or crimped to form a number of tablets or particulates, such as, for example, those shown in FIG. 1, where the adverse agent-containing core is substantially or completely enveloped by the sheath layer(s) and the shell layer(s). Advantageously, in a preferred embodiment, the action of a rolling punch device crimps or pinches the shell and sheath layers such that the sheath substantially or completely surrounds the core and the shell substantially or completely surrounds the sheath. In any case, the compositions of the core and the sheath should be formulated accordingly to limit or prevent the rate of in vivo release of the sequestered adverse agent.

In addition, it is to be understood that the tablets or particles can be any geometrical shape within a desired size range, such as a bead, a seed, a pellet, etc., depending the method of producing the tablets or particulates from the co-extruded multilayer sheet or laminate. For example, where oral dosage forms are desired, the shape can include, but is not limited to, spherical, ellipsoidal, cylindrical, modified cylindrical (e.g., having cylindrical sides with top and/or bottom curvature; having a substantially flat top and/or bottom with the sides having some degree of curvature, or a combination thereof), oval, elliptical, or the like, or some combination thereof, where "cylindrical" can include not only circular cross-sections but also one or more of the following cross-sections: triangular, square, rhomboidal, diamond, trapezoidal, pentagonal, hexagonal, octagonal, star-shaped (e.g., having 3, 4, 5, 6, or more points), or some combination thereof, including those shapes where the corners have been at least partially rounded. In one embodiment, the particulates formed can be ellipsoidal with dimensions (height, length, and width) from about 0.1 mm to about 3.0 mm. In another embodiment, the particulates formed can be cylindrical with similar dimensions. In one embodiment, the tablets or particles are hexagonal. The rendering of hexagonal tablets or particles from an extrudable sheet can allow for a reduction in waste as compared to, for example, round tablets or particles.

It will be apparent to one of ordinary skill in the art of pharmaceutical extrusion that the compositions and dimensions of the core, the optional sheath, and shell can be varied to achieve the desired release rate of the active agent and to adequately sequester the adverse agent. For example, by changing the co-extrusion die exit orifice dimensions, the thickness of the core, sheath and shell can be varied. In one embodiment, the thickness of the core, the optional sheath and the shell can be adjusted to provide a particle with a maximum dimension of about 5.0 mm or less; in another embodiment, from about 3.0 mm or less. In certain embodiments, the thickness of the core, the sheath and the shell is from about 0.05 mm to about 3.0 mm; in another embodiment, from about 0.2 mm to about 1.0 mm. The desired thickness of the sheath can be determined, for example, by the dissolution rate of the hydrophobic matrix material and the thickness of the core. In one embodiment, the thickness of the sheath is from about 0.05 mm to about 3.0 mm; in another embodiment, from about 0.1 mm to about 1.0 mm. The thickness of the shell can be adjusted based upon, for example, the shell composition and desired rate of release of the active agent. In one embodiment, the thickness of the shell is from about 0.05 mm to about 3.0 mm; in another embodiment, from about 0.1 mm to about 1.0 mm. In one embodiment, the dosage form can comprise a plurality of particles having a size ranging from about 0.1 mm to about 3.0 mm in any dimension.

In one embodiment, the dosage form comprises a plurality of MEM's. Optionally, following cutting and/or punching, the particles can be passed through a separator, for example, using #16 TBC (approximately 0.054") and #26 TBC (approximately 0.031") opening screens, and collected. In one embodiment, the particles are placed in hard or soft gelatin capsules for oral dosage to patients.

Figure 1B:
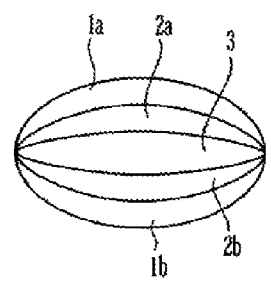
Figure 1C:
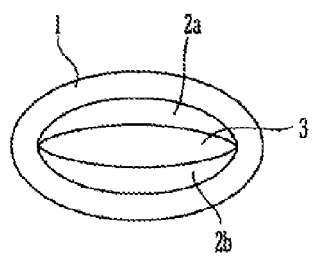

FIGS. 1a, 1b and 1c illustrate perspective views of three embodiments of a co-extruded particle of the present invention. In each of FIGS. 1a, 1b and 1c, core 3 comprises an adverse agent and a hydrophobic material. In FIG. 1a, sheath 2, which comprises a hydrophobic material, completely covers and surrounds core 3. Shell 1 comprises an active agent and a hydrophobic material, and completely covers and surrounds sheath 2.

In the embodiment shown in FIG. 1b, the sheath 2 comprises upper sheath component 2a and lower sheath component 2b. The sheath 2 surrounds the top and the bottom portions of core 3, but leaves a small amount of core 3 exposed along the side of the particle. Similarly, the shell 1 comprises uppers shell component 1a and lower shell component 1b. Shell 1 surrounds the top and the bottom of the sheath 2 while leaving a small portion of the sheath 2 and/or the core 3 exposed along the side of the particle.

In FIG. 1c, the sheath 2 comprises upper sheath component 2a and lower sheath component 2b which surround the top and the bottom of core 3 while leaving a small portion of core 3 exposed along the side. In this embodiment, the shell 1 completely covers and surrounds both sheath 2 and core 3.

FIG. 2 shows a non-limiting example of one method of forming the dosage form of the invention comprising the use of a rolling punch to render the multilayer extrudate into a plurality of particles. As illustrated in FIG. 2, a co-extruded multilayer extrudate sheet 16 exits the co-extrusion die. The multilayer extrudate comprises a core 3 comprising an adverse agent, a sheath 2 comprising a hydrophobic material and a shell 1 comprising an active agent. The multilayer extrudate 16 is conveyed from the co-extrusion die exit orifice to a rolling punch 10 which renders the multilayer extrudate 16 into a plurality of particles 14. In certain embodiments, the shell and sheath are pinched or crimped by the rolling punch to substantially encapsulate the core, thus creating an ellipsoid-shaped multilayer particle. In certain embodiments, including but not limited to, where the multilayer extrudate is simply cut or is incompletely punched and crimped, an exposed area of the core and/or sheath can exist, such as at the sides or edges of the dosage form or particle.

6. METHODS FOR ADMINISTRATION

The present invention is also directed to methods for treating a condition in a patient including administering a dosage form of the present invention to a patient in need of said treatment. The dosage form, can be, for example, an oral dosage form, such as a tablet or capsule, or a rectal or vaginal dosage form, such as a suppository. In one embodiment, the condition is pain and the dosage form includes an opioid and a sequestered opioid antagonist. In certain embodiments, the dosage form is administered to a patient twice a day, and in other embodiments, once a day.

6.1 Amount Per Dosage Unit

In the dosage form of the present invention, the amount of the active agent per dosage unit is that which is an effective amount for its particular indication and is independent of the amount of the adverse agent. For example, if the therapeutic agent is an opioid agonist, the amount of the opioid agonist in the dosage form of the present invention is generally from about 1 mg to about 800 mg; in one embodiment from about 5 mg to about 160 mg. One of ordinary skill in the art can readily determine, without undue experimentation, the amount of therapeutic agent needed for a particular indication.

The amount of the adverse agent in the dosage form of the present invention is such that the adverse agent can give the intended adverse effect if, when tampered with, a substantial amount of the adverse agent is released immediately from the dosage form and absorbed into an animal's blood. When, upon tampering with the dosage form, the adverse agent is intended to reduce or eliminate one or more of the pharmacological effects of the active agent, such as euphoria, the amount of the adverse agent in the dosage form is at least sufficient to reduce or eliminate those effects of the active agent when both agents are substantially or completely released from the dosage form and absorbed into an animal's blood after tampering has occurred.

When the adverse agent is an opioid antagonist, such as naltrexone or nalmefene, the amount of the opioid antagonist present in a dosage form of the present invention can be from about 0.5 mg to about 50 mg. The opioid antagonists cyclazocine and naltrexone, when administered orally, retain much of their efficacy with a long duration of action, approaching 24 hours. Amounts of less than about 10 mg of these opioid antagonists are typically used in oral formulations of the invention.

When, upon tampering, the adverse agent is intended to cause an undesired physiological reaction, such as emesis, the amount of the adverse agent in the dosage form is at least sufficient to cause such effect upon release after tampering has occurred.

For safety reasons, the amount of the adverse agent present in the dosage form should elicit the intended adverse effect without being harmful to humans even if it is all immediately released.

In certain embodiments of the present invention, the ratio of the therapeutic agent to the adverse agent in the dosage form can be from about 1:1 to about 50:1 by weight, in one embodiment from about 1:1 to about 20:1 by weight. In certain other embodiments, the ratio can be about 1:1 to about 10:1 by weight.

In non-limiting embodiments in which the opioid agonist is hydrocodone, the controlled release dosage forms can include analgesic doses from about 5 mg to about 80 mg of hydrocodone per dosage unit. In non-limiting embodiments where the opioid agonist is hydromorphone, it can be included in an amount from about 2 mg to about 64 mg hydromorphone hydrochloride per dosage unit. In non-limiting embodiments in which the opioid agonist is morphine, it can be present in the dosage form from about 2.5 mg to about 800 mg morphine per dosage unit. In non-limiting embodiments in which the opioid agonist is oxycodone, the dosage forms can include from about 2.5 mg to about 160 mg oxycodone, and in another embodiment from about 20 mg to about 30 mg oxycodone per dosage unit. Controlled-release oxycodone formulations are known in the art. In a non-limiting embodiment, the opioid agonist can be tramadol in an amount from about 25 mg to 800 mg tramadol per dosage unit. The dosage form can contain more than one opioid agonist, and the doses of each can be adjusted accordingly.

The term "unit dose" is defined for purposes of the present invention as the total amount of dosage form needed to administer a single desired dose of active agent (e.g., opioid agonist) to a patient.

6.2 Methods for Vaginal or Rectal Administration

As noted above, the present invention is also directed to administration of a dosage form comprising an active agent and an adverse agent, which can be sequestered, to a patient in need thereof in the form of a suppository for absorption through the vagina or rectum. When administered as a suppository, the composition preferably includes a suppository base material. Any suppository base material can be used provided it does not dissolve the particulates. For example, cocoa butter is a traditional suppository base material, which can be modified by the addition of waxes to raise its melting point. One or more water-miscible suppository base materials, such as polyethylene glycols of various molecular weights, can be included. When administered as a suppository, the combined concentration of the first and second plurality of particles in the suppository formulation is, typically, from about 5% to about 80% by weight of the composition.

6.3 Kits

The present invention is also directed to a kit containing at least one dosage form of the invention. In one embodiment, the dosage form is present in a container, e.g., a bottle or box. In another embodiment, the kit further includes a set of instructions directing the use of the dosage form to treat a patient, e.g., for pain. In one embodiment, the instructions can be a printed label affixed to or printed on the container. In another embodiment, the instructions can include a printed sheet inserted into the container or into the packaging which contains the container. The instructions can also state that the dosage form and/or its usage are designed to reduce abuse, misuse or diversion of the dosage form.

7. EXAMPLES

The following example is set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the present invention.

7.1 Example 1: Preparation of Particles Containing Opioid Agonist and Sequestered Opioid Antagonist by Melt Co-Extrusion Example 1 describes a prophetic example of a process which should be suitable for the preparation by melt co-extrusion of a particle including a core comprising an opioid antagonist, a sheath, and a shell comprising an opioid agonist. The active agent is hydromorphone hydrochloride and the sequestered opioid antagonist is naltrexone hydrochloride. The top and bottom of the core is covered by a sheath which does not contain any hydromorphone or naltrexone. The formulations of the feed to the core extruder, the sheath extruder and the shell extruder are provided in Table 1.

TABLE 1

| Formulation Used to Prepare Sheathed Sequestered Naltrexone Hydrochloride Particles by Melt Co-extrusion. | |
|---|---|
| Ingredient | Amount (mg) |
| Core Formulation: | 67 |
| Naltrexone HCl | 8 |
| EUDRAGIT RS PO ™ | 44 |
| Stearyl alcohol | 7 |
| Stearic acid | 7 |
| BHT | 1 |
| Sheath Formulation: | 59 |
| EUDRAGIT RS PO ™ | 44 |
| Stearyl alcohol | 15 |
| Shell Formulation: | 120 |
| Hydromorphone HCl | 12 |
| EUDRAGIT RS PO ™ | 76.5 |
| Stearyl Alcohol | 27 |
| Ethyl cellulose | 4.5 |
| Total | 246 |

The multilayer particle of Example 1 can be prepared by charging the formulation ingredients for the core, the sheath and the shell into three separate extruders. For example, each formulation can be charged to the powder-feeder hopper of a Leistritz twin screw extruder having a vacuum attachment. Each extruder can be equipped with twin-screws and a multi-zone heated barrel. In each extruder, the initial zones, intermediate and final zones can be maintained at a target temperature of about 30° C. to about 150° C. Each extruder can be allowed to thermally equilibrate for about 30 minutes. The inside pressure of each twin screw extruder can be maintained from about 600 to about 980 mbar negative. The inlet of each extruder barrel is attached to the outlet end of the respective powder-feeder hopper. The outlet of the separate core, sheath and shell extruder barrels can be connected to the appropriate inlet orifice of a co-extrusion die to form a multilayer extrudate sheet or laminate. The rotation speed of each extruder can be set to a level to produce the desired combined output, at the die orifice, such as about 5 to 15 kg/hr. The formulations can be heated with mixing until respective molten masses form. Each resultant viscous mass can then be extruded through the respective extruder barrel to the respective co-extrusion die inlet ports to form the multilayer extrudate sheet containing the core, the sheath and the shell. The multilayer extrudate sheet can then be transported on a continuous movable belt to a rolling punch device as it partially cools and congeals. In one embodiment, the partially congealed hardened multilayer sheet can be pelletized with a rolling punch device into hexagonal particles each having a major axis diameter of about 0.1 to about 3.0 mm, a minor axis diameter of about 0.1 to about 3.0 mm, and a thickness of about 0.1 to about 3.0 mm. In these particles, the average thickness of the core can be about 0.05 to about 3.0 mm; the average thickness of the sheath can be about 0.05 to about 3.0 mm; and the average thickness of the shell can be about 0.05 to about 3.0 mm.

The in vitro rate of dissolution of the dosage form can be measured using the USP basket method. The apparatus can consist of a USP Type 1 basket (100 rpm). The particulate dosage forms are contacted with 700 mL simulated gastric fluid (SGF), (pH 1.2 without enzyme) at 37° C. for one hour. Thereafter, the particulate dosage forms are contacted with 900 mL simulated intestinal fluid (SIF) (pH 7.5 without enzyme) for the duration of the test. The rate of dissolution is determined by assaying each of the fluids using HPLC.

The amount of adverse agent released in vivo is expected to be less than an amount which will significantly affect the pharmaceutical effect of the active agent and less than an amount which will elicit any significant unpleasant physiological effects.

All patents, applications, publications, test methods, literature, and other materials cited above are hereby incorporated herein by reference in their entirety for all purposes.

What is claimed is:

1. A co-extruded dosage form comprising a plurality of co-extruded multilayer extrudates, each extrudate comprising:
    an extruded core comprising a matrix of an adverse agent and a hydrophobic material, wherein the hydrophobic material is present in an amount of about 30 wt % to about 99 wt % of the extruded core;
    an extruded sheath comprising a hydrophobic material which surrounds at least a portion of the core, wherein the sheath is free of an adverse agent and free of an active agent, wherein the hydrophobic material is present in an amount of about 10 wt % to about 99 wt % of the extruded sheath; and
    an extruded shell comprising an active agent and a hydrophobic material which surrounds at least a portion of the sheath, wherein the hydrophobic material is present in an amount of about 1 wt % to about 80 wt % of the extruded shell, and wherein the shell has a thickness of about 0.05 mm to about 3 mm;
    wherein each extrudate is a portion of a multilayer extrudate sheet; and
    wherein the dosage form releases about 10% or less adverse agent over a 36 hour period when subjected to an in-vitro dissolution test using USP Basket Method at 100 rpm in 700 ml simulated gastric filled at pH 1.2 without enzyme at 37° C. for 1 hour followed by 900 ml simulated intestinal fluid at pH 7.5 without enzyme for the duration of the test.

2. The co-extruded dosage form of claim 1, wherein the sheath surrounds a majority of the core; and the shell surrounds a majority of the sheath.

3. The co-extruded dosage form of claim 1, wherein each hydrophobic material independently comprises a material selected from the group consisting of acrylic and methacrylic acid polymers and copolymers, alkylcelluloses, natural and synthetic waxes, water insoluble waxes, fatty alcohols, fatty acids, hydrogenated fats, fatty acid esters, fatty acid glycerides, hydrocarbons, hydrophobic and hydrophilic polymers having hydrocarbon backbones, and mixtures of any two or more of the foregoing.

4. The co-extruded dosage form of claim 3, wherein the hydrophobic material in the core comprises an ammonio methacrylate copolymer.

5. The co-extruded dosage form of claim 1, wherein the dosage from is an oral dosage form.

6. The co-extruded dosage form of claim 5, wherein the oral dosage form is a tablet or caplet.

7. The co-extruded dosage of claim 5, wherein the oral dosage form is a capsule containing a plurality of co-extruded particles.

8. The co-extruded dosage form of claim 1, wherein the active agent is an opioid agonist and the adverse agent is an opioid antagonist.

9. The co-extruded dosage form of claim 1, wherein the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacyl morphan, lofentanil, meperidine, meptazinol, metazocine, methadone, metophon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tramadol, tilidine, pharmaceutically acceptable salts thereof, and mixtures of any two or more of the foregoing.

10. The co-extruded dosage form of claim 1, wherein the opioid agonist is selected from the group consisting of morphine, codeine, hydromorphone, hydrocodone, oxycodone, oxymorphone, dihydrocodeine, dihydromorphine, pharmaceutically acceptable salts thereof, and mixtures of any two or more of the foregoing.

11. The co-extruded dosage form of claim 8, wherein the opioid antagonist is selected from the group consisting of cyclazocine, naloxone, naltrexone, nalmefene, nalbuphine, nalorphine, cyclazacine, levallorphan, pharmaceutically acceptable salts thereof, and mixtures of any two or more of the foregoing.

12. The co-extruded dosage form of claim 8, wherein the opioid antagonist is selected from the group consisting of naloxone, naltrexone, nalmefene, pharmaceutically acceptable salts thereof, and mixtures of any two or more of the foregoing.

13. The co-extruded dosage form of claim 8, wherein the dosage form provides controlled release of the opioid agonist following administration to a patient.

14. The co-extruded dosage form of claim 8, wherein the dosage form releases about 0.5 mg or less of the opioid antagonist in vivo following administration to a patient.

15. The co-extruded dosage form of claim 8, wherein the dosage form releases about 0.05 mg or less of the opioid antagonist in vivo following administration to a patient.

16. A method for treating pain in a patient, comprising administering a co-extruded dosage form according to claim 1 to a patient, wherein the active agent is an opioid agonist and the adverse agent is an opioid antagonist.

17. A co-extruded dosage form comprising:
    a plurality of co-extruded multilayer extrudates, each extrudate comprising:
        an extruded core comprising a matrix of an adverse agent and a hydrophobic material;
        an extruded sheath comprising a hydrophobic material which surrounds at least a portion of the core, wherein the sheath is free of an adverse agent and free of an active agent; and
        an extruded shell comprising an active agent and a hydrophobic material which surrounds at least a portion of the sheath, wherein the extruded shell has a thickness of about 0.05 mm to about 3 mm;
    wherein each extrudate is a portion of a multilayer extrudate sheet,
    wherein each of the plurality of particles is from about 0.05 mm to about 3.0 mm in all dimensions,
    wherein the dosage form releases about 10% or less adverse agent over a 36 hour period when subjected to an in-vitro dissolution test using USP Basket Method at 100 rpm in 700 ml simulated gastric filled at pH 1.2 without enzyme at 37° C. for 1 hour followed by 900 ml simulated intestinal fluid at pH 7.5 without enzyme for the duration of the test.

* * * * *